US008193516B2

(12) United States Patent  
Kimura

(10) Patent No.: US 8,193,516 B2  
(45) Date of Patent: Jun. 5, 2012

(54) SENSING APPARATUS

(75) Inventor: Toshihito Kimura, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 588 days.

(21) Appl. No.: 12/392,703

(22) Filed: Feb. 25, 2009

(65) Prior Publication Data

US 2009/0218499 A1     Sep. 3, 2009

(30) Foreign Application Priority Data

Feb. 28, 2008  (JP) ................ 2008-047613

(51) Int. Cl.
 *G01N 21/35* (2006.01)
(52) U.S. Cl. .................................... 250/458.1
(58) Field of Classification Search ............. 250/458.1
 See application file for complete search history.

(56) References Cited

U.S. PATENT DOCUMENTS

| 6,570,657 | B1 * | 5/2003 | Hoppe et al. ............ 356/445 |
| 2002/0028519 | A1 * | 3/2002 | Yguerabide et al. ....... 436/518 |
| 2005/0200852 | A1 | 9/2005 | Kimura |
| 2006/0012795 | A1 | 1/2006 | Niemax et al. |
| 2006/0023221 | A1 * | 2/2006 | Kimura .................. 356/445 |
| 2006/0170918 | A1 * | 8/2006 | Nishiuma ............... 356/318 |
| 2007/0008546 | A1 | 1/2007 | Ho et al. |

FOREIGN PATENT DOCUMENTS

| JP | 07-229845 A | 8/1995 |
| JP | 10-078390 A | 3/1998 |
| JP | 2001-021565 A | 1/2001 |
| JP | 2002-062255 A | 2/2002 |
| JP | 2002-257731 A | 9/2002 |
| JP | 2003-185568 A | 7/2003 |
| JP | 2007-114156 A | 5/2007 |
| JP | 2007-225389 A | 9/2007 |
| WO | 00/70328 A1 | 11/2000 |
| WO | 02/054071 A1 | 7/2002 |

OTHER PUBLICATIONS

EP Communication, dated May 25, 2009, issued in corresponding EP Application No. 09002700.4, 7 pages.
Communication pursuant to Article 94(3) EPC, dated Feb. 3, 2012, issued in corresponding EP Application No. 09 002 700.4, 6 pages.
Notification of Reasons for Refusal, dated Feb. 7, 2012, issued in corresponding JP Application No. 2008-047613, 6 pages in English and Japanese.

\* cited by examiner

*Primary Examiner* — Constantine Hannaher
(74) *Attorney, Agent, or Firm* — Sughrue Mion, PLLC

(57) ABSTRACT

A sensing apparatus includes a prism, a metal film provided on a surface of the prism, a substrate that is provided on a surface of the prism and which has formed therein a channel for supplying a sample to the metal film, a light source for issuing light, an optical unit for incident light by which the light being issued from the light source is launched into the prism at such an angle that the light is totally reflected on a boundary surface between the prism and the metal film, the optical unit for incident light including a light intensity distribution adjusting section that reduces difference between the maximum and the minimum values in the intensity distribution of the light that is launched into the prism, and a light detecting unit for detecting the light that is generated in neighborhood of the metal film.

5 Claims, 9 Drawing Sheets

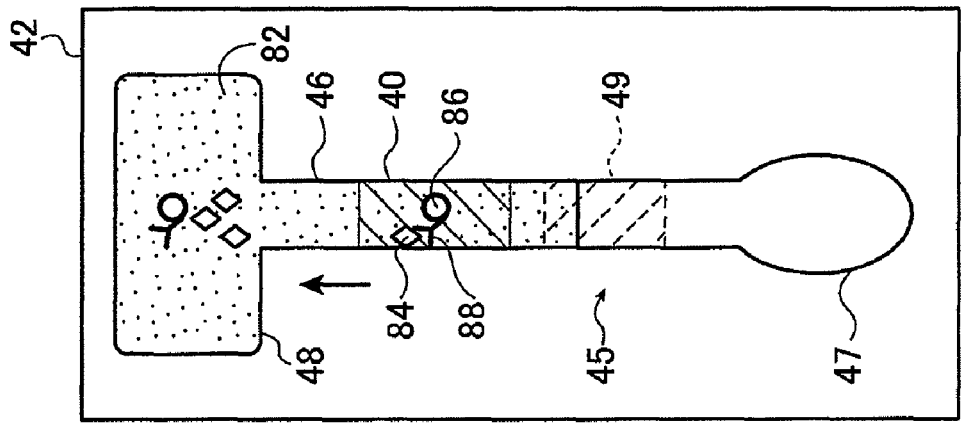
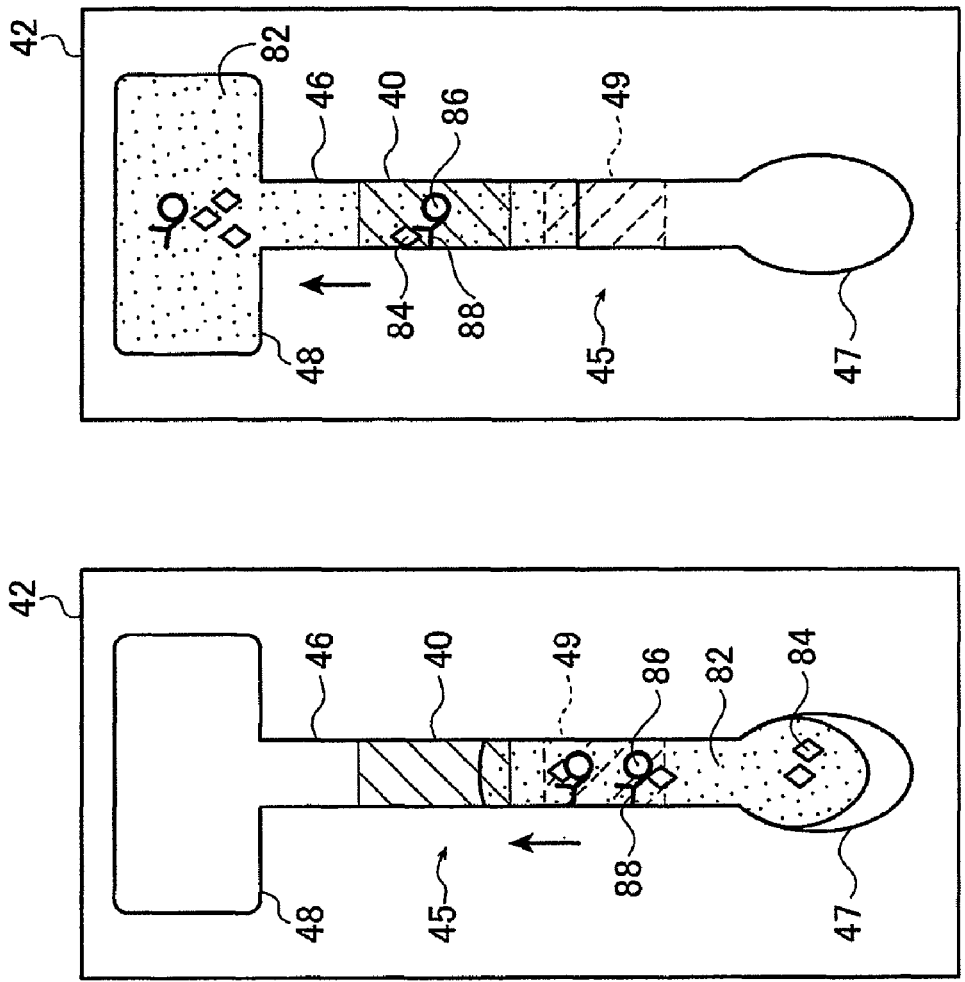
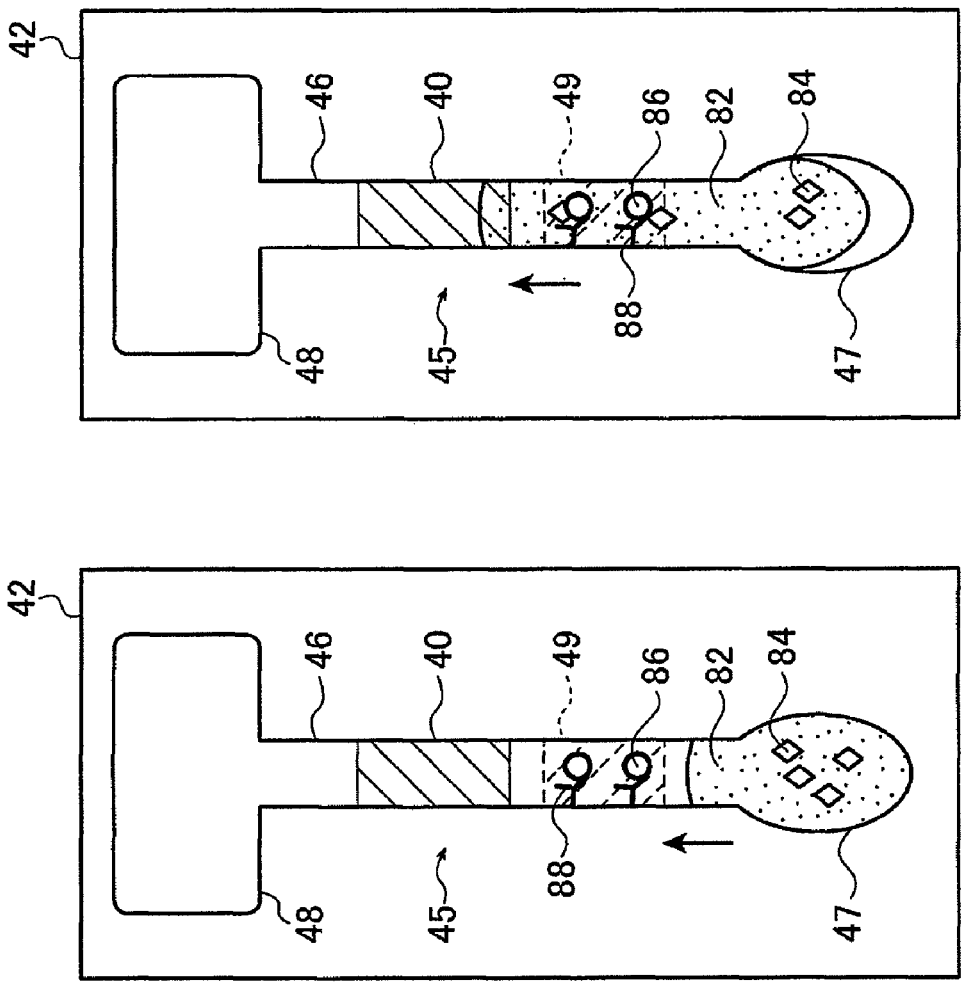

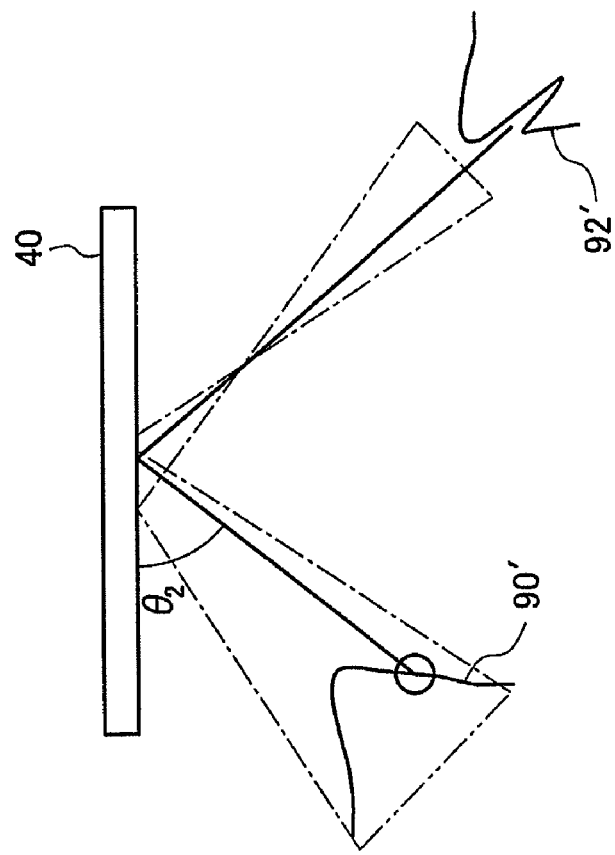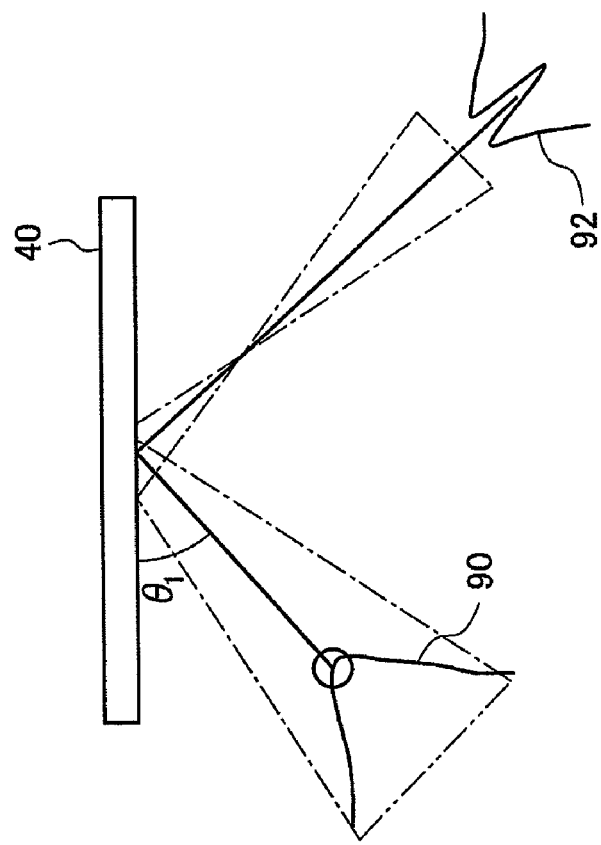

SENSING APPARATUS

The entire contents of documents cited in this specification are incorporated herein by reference.

BACKGROUND OF THE INVENTION

The present invention relates to a sensing apparatus that detects analytes with the aid of an enhanced field created by allowing light to strike a detection surface at a specified angle of incidence.

Known as a method that can be used in bio-measurement (measurement of reactions in biomolecules) and the like to detect (or measure) analytes with high sensitivity and great ease is fluorometry in which fluorescence from a fluorescent material that is excited by light at a specified wavelength to emit fluorescence (i.e., a fluorescence emitting material) is detected to thereby detect (or measure) the analytes.

If the analytes in fluorometry are a fluorescent material, a sample of interest that is assumed to contain the analytes is irradiated with exciting light at a specified wavelength and the resulting emission of fluorescence is detected to verify the presence of the analytes.

Even if the analytes in fluorometry are not a fluorescent material, a specifically binding material, or a material that specifically binds to the analytes is labeled with a fluorescent material and then bound to the analytes; subsequently, the same procedure as described above is performed to detect fluorescence (specifically, the fluorescence from the fluorescent material with which the specifically binding material that has bound to the analytes is labeled), whereby the presence of the analytes is verified.

It has been proposed that the sensitivity of analyte detection in fluorometry be increased by exciting the fluorescent material with the aid of an enhanced electric field that results from surface plasmon resonance on a metal film (see, for example, JP 2002-62255 A, JP 2001-21565 A, and JP 2002-257731 A).

In each of the methods described in those patent documents, analytes labeled with a fluorescent material are positioned in the neighborhood of a thin metal film and light is allowed to strike the boundary surface between the thin metal film and a prism (either a semicylindrical or triangular glass prism) at an angle that satisfies the plasmon resonance condition (plasmon resonance angle) to create an enhanced electric field on the thin metal film so that the analytes in the neighborhood of the thin metal film are excited strong enough to amplify the emission of fluorescence from the fluorescent material. This is a method of fluorescence detection utilizing the surface plasmon enhanced fluorescence (which is hereinafter sometimes abbreviated as SPF).

As described in JP 2001-21565 A, the electric field of surface plasmons is highly localized on the metal surface and attenuates exponentially with the distance from the metal surface, so fluorescently labeled antibodies (i.e., the fluorescent material) adsorbed onto the metal surface can be excited selectively and with high probability. As also described in JP 2001-21565 A, this SPF-based version of fluorescence detection ensures that the effect of any interfering material that is distant from the interface is suppressed to the smallest level, which also allows for precise detection of the analytes.

JP 2001-21565 A and JP 2002-257731 A also describe a rotating mechanism that adjusts the angle of the prism that bears the metal film; the angle of the prism is adjusted by this rotating mechanism so that the light issued from the light source is allowed to be launched into the prism at an optimum plasmon resonance angle.

The method of detecting analytes by making use of the surface plasmon enhancing effect is not limited to detecting the fluorescence excited by surface plasmons and another method that can be adopted is by detecting scattered light.

JP 10-78390 A describes a surface plasmon sensor comprising a prism, a metal film formed on a surface of the prism, a functional thin film that is provided on a surface of the metal film to trap analytes by an antigen-antibody reaction, and a flow cell that supplies a sample liquid as it makes contact with the functional thin film.

The operating principle of this surface plasmon sensor is such that the electric field of surface plasmons as excited by making use of the surface plasmon enhancing effect on the metal film is disturbed by the analytes present on the functional thin film to generate scattered light, which is detected to eventually detect the analytes. Thus, the method that detects scattered light rather than fluorescence can also be utilized to detect analytes.

SUMMARY OF THE INVENTION

Here, the plasmon resonance condition of surface plasmons varies with the wavelength of the illuminating light, the angle of incidence on the metal film, the refractive index and asperities of the prism, the dielectric constant of the metal film, its thickness, the degree of its denseness, the type of the sample to be positioned on the metal film, its state, and other factors. However, the methods described in JP 2001-21565 A and JP 2002-257731 A, which, with a view to achieving detection at a maximum degree of enhancement with high reproducibility, provide the rotating mechanism and use it to rotate both the substrate and the prism for detecting an optimum angle, have had the problems of higher apparatus cost and the tendency of the fluorescent material on the metal film to emit a smaller quantity of fluorescence in the process of detecting the optimum angle.

Instead of providing the mechanism for adjusting the incident angle of light, one may think of performing temperature adjustment for assuring the above-mentioned physical constants and relative positions (i.e., keeping them constant) as well as making the shapes of individual members identical to one another; however, this increases the costs of the apparatus and the chip producing facilities and, hence, is unacceptable for use in blood diagnosis applications where the demand for cost reduction is particularly rigorous.

These problems have contributed to preventing commercial use of the plasmon-based sensing apparatus.

In contrast, according to the SPF-based methods of fluorescence detection that are described in JP 2002-62255 A, JP 2001-21565 A and JP 2002-257731 A as well as the method described in JP 10-78390 A that detects the scattered light resulting from the disturbing of surface plasmons by the analytes, the light issued from the light source is condensed by lenses and the like to have a specified angular range before it is allowed to be incident on the metal film, whereby it becomes unnecessary to perform an angular adjustment within the angle of convergence, thus contributing to cost reduction.

However, the light issued from the light source varies in intensity with the position of an individual ray of light (e.g., the distance from the center of the light beam), namely, it has an intensity distribution; this poses a problem in that the angle at which surface plasmon resonance occurs changes and so does the intensity of the electric field created by surface plasmons.

In addition, the fluorescence from fluorescent materials, even if they are identical to each other, varies with the intensity of the electric field created by surface plasmons, and if the intensity of the electric field created by surface plasmons changes, the quantity of fluorescence from the same amount of two identical fluorescent materials changes and so does the detected value; as a result, the precision of detection drops and so does reproducibility.

The difficulties are in no way limited to the case of detecting analytes with the aid of the electric field created by surface plasmons and the same problems occur if one attempts to detect analytes with the aid of an enhanced field that is generated by allowing light to strike a detection surface at a specified angle of incidence.

An object, therefore, of the present invention is to solve the aforementioned problems with the prior art by providing a sensing apparatus that can detect the analytes in a sample with high precision and reproducibility.

A sensing apparatus according to the invention comprises: a prism; a metal film provided on a surface of the prism; a substrate that is provided on a surface of the prism and which has formed therein a channel for supplying the sample to the metal film; a light source for issuing light; an optical unit for incident light by which the light being issued from the light source is launched into the prism at such an angle that the light is totally reflected on a boundary surface between the prism and the metal film, the optical unit for incident light including a light intensity distribution adjusting section that reduces difference between the maximum and the minimum values in the intensity distribution of the light that is launched into the prism; and a light detecting means for detecting the light that is generated in neighborhood of the metal film.

BRIEF DESCRIPTION OF THE DRAWINGS

FIGS. 4A to 4C are illustrations showing how a sample flows in the sample unit;

FIGS. 8A and 8B are diagrams each showing the relationship between the intensity of conventional exciting light and the condition for the occurrence of surface plasmon resonance;

DESCRIPTION OF THE PREFERRED EMBODIMENTS

The sensing apparatus of the present invention is described on the following pages by referring to the embodiments shown in the accompanying drawings.

Figure 1:
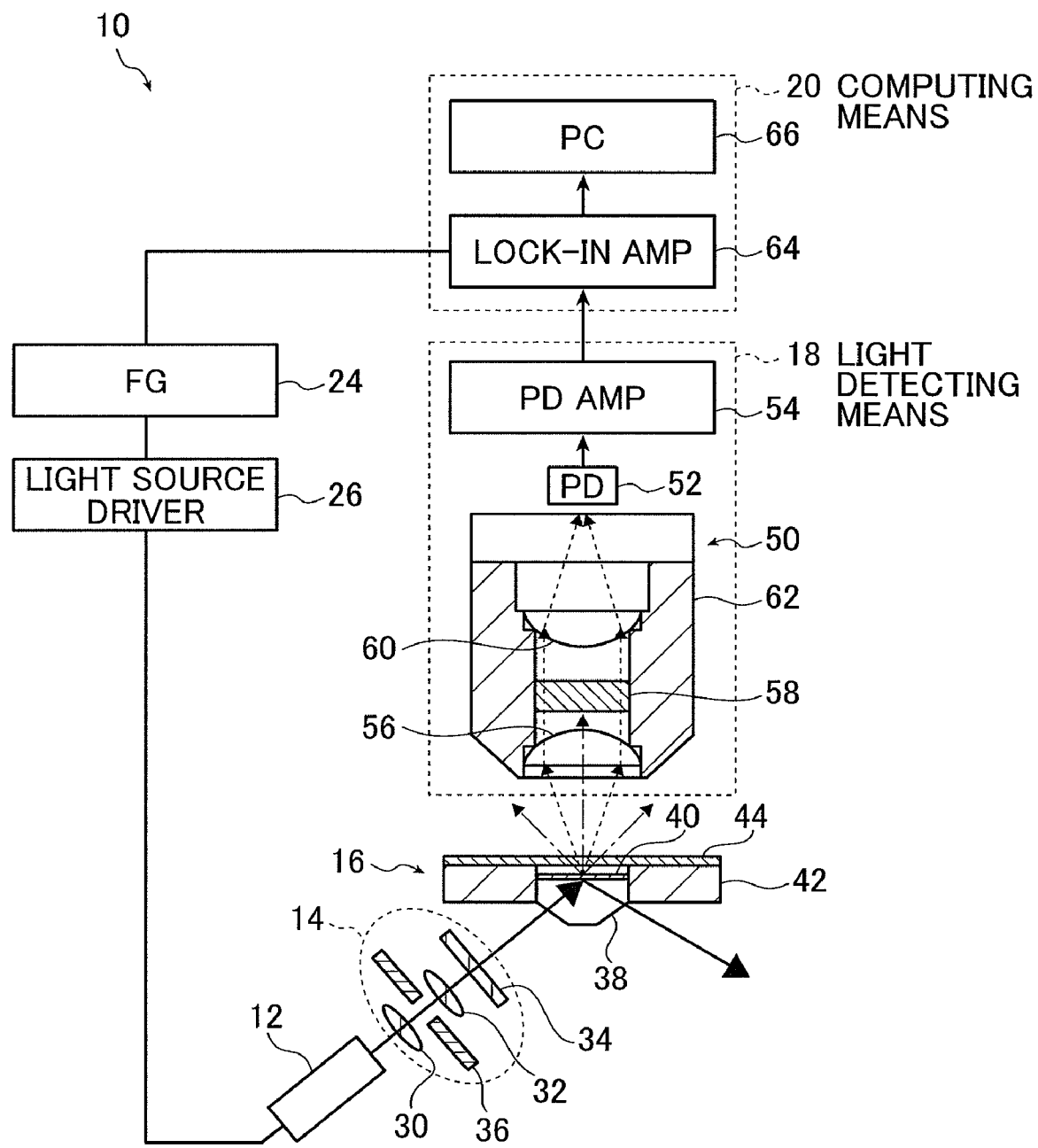
FIG. 1 is a block diagram showing a general construction of an embodiment of the sensing apparatus of the present invention.
Figure 2A:
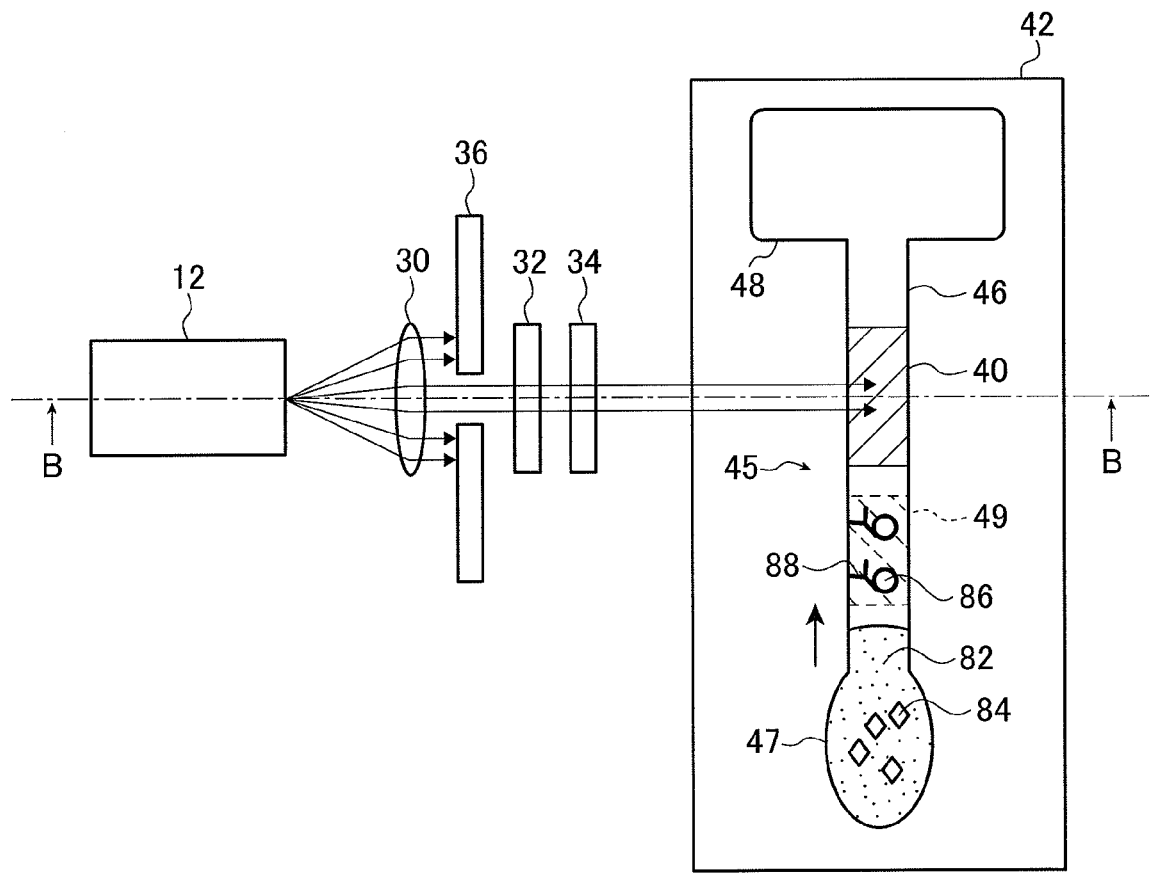
FIG. 2A is a top view showing a general layout of a light source, an optical unit for incident light, and a sample unit in the sensing apparatus shown in FIG. 1.
Figure 2B:
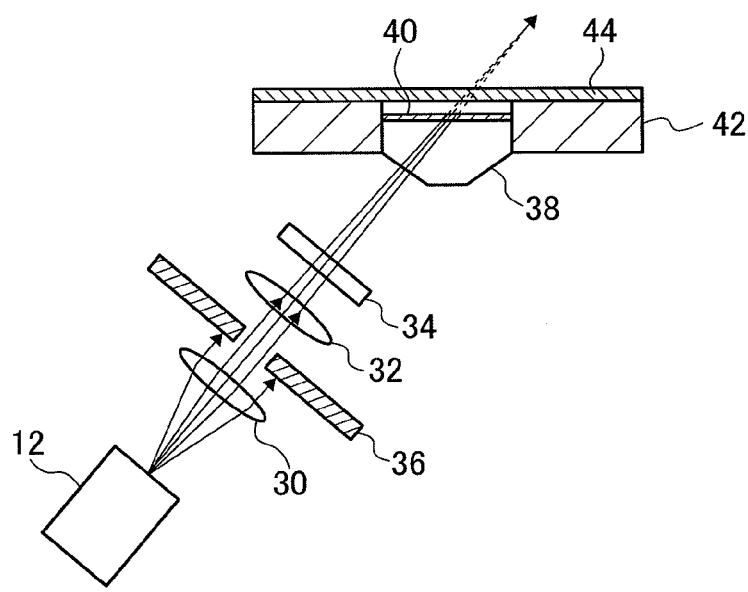
FIG. 2B is a section of FIG. 2A taken along line B-B.
Figure 3:
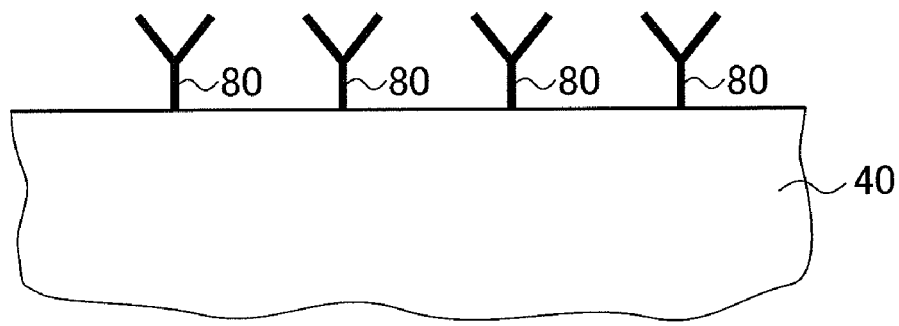
FIG. 3 is an enlarged schematic view showing enlarged a part of the metal film on the sample unit shown in FIGS. 2A and 2B.

FIG. 1 is a block diagram showing a general construction of a sensing apparatus 10 which is an embodiment of the sensing apparatus of the present invention; FIG. 2A is a top view showing a general layout of a light source 12, an optical unit for incident light 14, and a sample unit 16 in the sensing apparatus 10 shown in FIG. 1; and FIG. 2B is a section of FIG. 2A taken along line B-B. FIG. 3 is an enlarged schematic view showing enlarged a part of a metal film 40 on the sample unit 16 shown in FIGS. 2A and 2B.

As shown in FIG. 1 as well as in FIGS. 2A and 2B, the sensing apparatus 10 comprises basically the light source 12 that issues light of a specified wavelength, the optical unit for incident light 14 that guides and condenses the light issued from the light source 12 (which is hereinafter sometimes referred to as the exciting light), the sample unit 16 that holds a sample (to be measured) 82 that contains analytes 84 and which is to be struck with the light condensed by the optical unit for incident light 14, a light detecting means 18 for detecting the light issued from a measurement position on the sample unit 16, and a computing means 20 which, on the basis of the result of detection by the light detecting means 18, detects the analytes 84 (namely, digitizes the signal as detected by the light detecting means 18, checks for the presence of the analytes, and determines their concentration if they are present); having this construction, the sensing apparatus 10 detects (and measures) the analytes 84 contained in the sample 82.

The sensing apparatus 10 further includes a function generator (hereinafter abbreviated as FG) 24 for modulating the exciting light, and a light source driver 26 by means of which an electric current proportional to the voltage generated in the FG 24 is flowed into the light source 12.

The FG 24 is a signal generator that generates repeating clocks at high and low voltages. When the FG 24 causes a signal to flow into the light source driver 26 which then supplies the light source 12 with an electric current proportional to the generated voltage, the light source 12 emits light as modulated in accordance with the clocks. The clocks from the FG 24 are inputted to a lock-in amplifier 64 which in turn picks up only the signal that is synchronous with the clocks from an output of the light detecting means 18.

Although not shown, the individual parts of the sensing apparatus 10 are supported by support mechanisms to fix their relative positions.

The light source 12 is a semiconductor laser issuing light at a specified wavelength.

The optical unit for incident light 14 comprises a collimator lens 30, a cylindrical lens 32, a polarizing filter 34, and a light shield plate 36 which are inserted into the optical path of the exciting light and arranged in the order of the collimator lens 30, light shield plate 36, cylindrical lens 32, and the polarizing filter 34, with the collimator lens 30 being the closest to the light source 12. Hence, the light issued from the light source 12 passes through the collimator lens 30, light shield plate 36, cylindrical lens 32, and the polarizing filter 34 in that order and is then launched into the sample unit 16.

The collimator lens 30 is a device by which the light issued from the light source 12 to diffuse radially through a specified angle is converted to parallel light.

As shown in FIGS. 2A and 2B, the cylindrical lens 32 is a columnar lens whose axis extends parallel to the length of the channel in the sample unit which will be described later; by means of this lens, the light that has been rendered parallel by passage through the collimator lens 30 is condensed to focus on only a plane normal to the axis of the column (a plane parallel to the paper on which FIG. 2B is drawn).

The polarizing filter 34 is a filter by which the light passing through it is P-polarized with respect to the reflecting surface of the sample unit 16 which will be described later.

The light shield plate 36 is a member in plate form that is provided in the optical path of the exciting light between the collimator lens 30 and the cylindrical lens 32 and whose center aligns with the center of the exciting light beam. The light shield plate 36 is formed of a non-light-transmitting material.

The light shield plate 36 blocks that portion of the light issued from the light source 12 which is more than a specified distance away from the center of the exciting light beam (i.e., the light that is outside the hole in the light shield plate 36). To be more specific, the light issued from the light source 12 diverges through the specified angle and the shield plate 36 blocks that portion of this light which has diverged through more than a certain angle (i.e., the light more than a certain distance away from the center of the light beam) but it allows passage of that portion of this light which has diffused through less than the certain angle (i.e., the light within the certain distance from the center of the light beam).

As regards the sample unit 16, it comprises a prism 38, a metal film 40, a substrate 42, and a transparent cover 44; the metal film 40 is formed on one surface of the prism 38 and a sample 82 containing the analytes 84 is placed on top of the metal film 40.

The prism 38 is generally in the form of a triangular prism with a cross section shaped like an isosceles triangle (to be more exact, the prism is in the form of a hexagonal cylinder as obtained by cutting off the apices of the isosceles triangle in cross section through a plane either normal or parallel to the base of the isosceles triangle); this prism is in the optical path of the light that is issued from the light source 12 and condensed by the optical unit for incident light 14.

The prism 38 is positioned in such a way that the light condensed by the optical unit for incident light 14 is incident on one of three sides that is defined by one of the two oblique sides of the isosceles triangle.

The prism 38 may be formed of a known transparent resin or optical glass; for example, it may be formed of ZEONEX® 330R (n=1.50; product of ZEON CORPORATION). However, in order to reduce the production cost, it is preferred to form the prism 38 of resins rather than optical glass; exemplary resins that may be used include polymethyl methacrylate (PMMA), polycarbonates (PC), and amorphous polyolefins (APO) containing cycloolefin.

Having this construction, the prism 38 allows the light condensed by the optical unit for incident light 14 to be incident on the surface that is defined by one of the two oblique sides of the isosceles triangle, the incident light being then reflected by the surface that is defined by the base of the isosceles triangle and emerging from the surface that is defined by the other of the two oblique sides of the isosceles triangle.

The metal film 40 is a thin metal film that is formed on part of that surface of the prism 38 which is defined by the base of the isosceles triangle (the part is specifically an area that includes the area that is illuminated with the light incident on the prism 38).

The metal film 40 may be formed of metals including Au, Ag, Cu, Pt, Ni and Al. If a liquid is used as the sample, Au or Pt is preferably used in order to suppress any reaction with the liquid.

The metal film 40 may be formed by a variety of methods; for example, it may be formed on the prism 38 by sputtering, evaporation, or plating.

In addition, as shown in FIG. 3, the metal film 40 has a plurality of primary antibodies 80 fixed to its surface as specific binding materials which specifically bind to the analytes 84.

The substrate 42 is a member in plate form that is provided on the surface of the prism 38 that is defined by the base of the isosceles triangle and, as shown in FIG. 2A, it has a channel 45 formed in its surface as a passage for feeding the sample 82 to the metal film 40.

The channel 45 consists of a straight linear portion 46 formed across and beyond the metal film 40, a beginning end portion 47 that is formed at one end of the linear portion 46 and serves as a liquid reservoir into which the sample 82 is fed during measurement, and a terminal end portion 48 that is formed at the other end of the linear portion 46 to serve as a liquid reservoir that is reached by the sample 82 that has passed through the linear portion 46 after being fed into the beginning end portion 47.

That part of the linear portion 46 which is closer to the beginning end portion 47 than the metal film 40 is provided with a secondary antibody placement area 49 where secondary antibodies 88 labeled with a fluorescent material 86 are placed.

The secondary antibodies 88 are each a specific binding material that specifically binds to the analyte 84.

The transparent cover 44 is a transparent member in plate form that is joined to that surface of the substrate 42 which is away from the surface in contact with the prism 38. By closing that surface of the substrate 42 which is away from the surface in contact with the prism 38, the transparent cover 44 seals the channel 45 formed in the substrate 42.

The transparent cover 44 has two openings formed in it, one in the area that corresponds to the beginning end portion 47 of the channel 45 and the other in the area that corresponds to its terminal end portion 48. If desired, the opening formed in the position that corresponds to the beginning end portion 47 (as well as the opening formed in the position that corresponds to the terminal end portion 48) may be provided with a lid that can be opened or closed.

Described above is the basic construction of the sample unit 16. It should be noted here that the prism 38 as well as the metal film 40 and the substrate 42 are preferably formed monolithically.

Here, the light source 12, the optical unit for incident light 14 and the sample unit 16 are arranged in such relative positions that the light emerging from the optical unit 14 to be launched into the prism 38 is totally reflected by the boundary surface between the prism 38 and the metal film 40 to emerge from the other surface of the prism 38.

The light detecting means 18 comprises an optical unit for detecting light 50, a photodiode (hereinafter PD) 52 and a photodiode amplifier (hereinafter PD amp) 54, and it detects light on the metal film 40 in the sample unit 16 (namely, the light emerging from the sample 82 on the metal film 40).

The optical unit for detecting light 50 comprises a first lens 56, a cut-off filter 58, a second lens 60, and a support member 62 that supports these members; it condenses the light emerging from the top of the metal film 40 (to be more exact, the neighborhood of the metal film 40) and allows it to be launched into the PD 52.

The first lens 56 is a collimator lens provided in a face-to-face relationship with the metal film 40; it renders parallel the light that has reached it after being emitted on the metal film 40.

The cut-off filter 58 has such a characteristic that it selectively cuts off a light component that has the same wavelength as the exciting light but transmits light components having different wavelengths than the exciting light (e.g., fluorescence originating from the fluorescent material 86); thus, the cut-off filter 58 transmits only those portions of the collimated light from the first lens 56 that have different wavelengths than the exciting light.

The second lens 60 is a condenser lens which condenses the light passing through the cut-off filter 58 and allows it to be launched into the PD 52.

The support member 62 is a holding member that holds the first lens 56, the cut-off filter 58 and the second lens 60 monolithically as they are spaced from each other.

The PD 52 is an optical detector that converts the received light to an electric signal; the light that has been condensed by the second lens 60 and launched into the PD 52 is converted to an electric signal. The PD 52 sends the electric signal to the PD amp 54 as a detection signal.

The PD amp 54 is an amplifier that amplifies detection signals, so it amplifies the detection signal coming from the PD 52 and sends the amplified detection signal to the computing means 20.

Comprising a lock-in amp 64 and a PC (e.g., an arithmetic section) 66, the computing means 20 computes the mass of the analytes, their concentration and the like from the detection signal.

The lock-in amp 64 is an amplifier that amplifies that component of the detection signal which has the same frequency as a reference signal, so it amplifies that component of the detection signal as amplified by the PD amp 54 which is synchronous with the reference signal sent from the FG 24. The detection signal amplified by the lock-in amp 64 is run (outputted) into the PC 66.

The detection signal fed into the PC 66 from the lock-in amp 64 is converted to a digital signal, based on which the PC 66 detects the concentration of the analytes in the sample. The concentration of the analytes in the sample can be computed from the relationship between the number of analytes and the liquid volume. The number of analytes can be computed from a calibration line that is constructed on the basis of the relationship between the intensity of the detection signal and the number of analytes as computed using a known number of analytes. Note that by feeding a constant liquid volume of the sample to the channel 45 in the substrate 42 of the sample unit 16 (or designing the sample unit 16 such that a constant volume of the sample will be fed), the concentration of the analytes can be computed in an easy but correct way.

Described above is the basic construction of the sensing apparatus 10.

Figure 5:
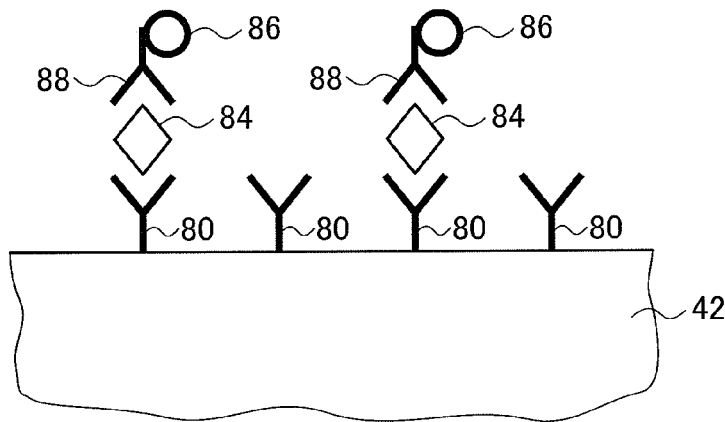
FIG. 5 is an enlarged schematic view showing enlarged a part of the metal film with the sample having reached it.

The present invention will be described below in greater detail by describing the action of the sensing apparatus 10. FIGS. 4A to 4C illustrate how the sample 82 flows in the sample unit 16, and FIG. 5 is an enlarged schematic view showing enlarged a part of the metal film 40 with the sample 82 having reached it.

First, as shown in FIG. 4A, the sample 82 containing the analytes 84 is dripped in the beginning end portion 47 of the channel 45 in the substrate 42 of the sample unit 16.

The sample 82 that has been dripped in the beginning end portion 47 starts to move towards the terminal end portion 48 through the tube defined by the linear portion 46 and the transparent cover 44 since it is shaped like a capillary tube.

The sample 82 moving from the beginning end portion 47 through the linear portion 46 towards the terminal end portion 48 will reach the secondary antibody placement area 49 of the linear portion 46, as shown in FIG. 4B. When the sample 82 reaches the secondary antibody placement area 49, the analytes 84 contained in the sample 82 enter into an antigen-antibody reaction with the secondary antibodies 88 placed in the secondary antibody placement area 49, whereupon the analytes 84 bind to the secondary antibodies 88. Since the secondary antibodies 88 have been labeled with the fluorescent material 86, the analytes 84 that have bound to the secondary antibodies 88 become labeled with the fluorescent material 86.

The sample 82 that has crossed the secondary antibody placement area 49 keeps moving through the linear portion 46 towards the terminal end portion 48 until it reaches the metal film 40. When the sample 82 has reached the metal film 40, the analytes 84 contained in the sample 82 enter into an antigen-antibody reaction with the primary antibodies 80 fixed on the metal film 40, whereby the analytes 84 are captured by the primary antibodies 80 (see FIG. 5). Since the analytes 84 captured by the primary antibodies 80 have already been labeled with the fluorescent material 86 in the secondary antibody placement area 49, the primary antibodies 80 that have captured the analytes 84 become labeled with the fluorescent material 86. In other words, the analyte 84 becomes sandwiched between the primary antibody 80 and the secondary antibody 88.

The sample 82 that has crossed the metal film 40 moves down to the terminal end portion 48. In addition, both the analytes 84 that have not been captured by the primary antibodies 80 and the secondary antibodies 88 that have not bound to the analytes 84, as well as the fluorescent material 86 labeling the secondary antibodies 88 also move down to the terminal end portion 48 together with the sample 82.

This leaves on the metal film 40 the analytes 84 that have bound to the secondary antibodies 88 so as to be labeled with the fluorescent material 86 (see FIG. 4C) and that have been captured by the primary antibodies 80.

As a result, only the secondary antibodies 88 labeled with the fluorescent material 86 and the analytes 84 immobilized together with the primary antibodies 80 are left on the metal film 40, which is then illuminated with the exciting light.

Specifically, the light source 12 is caused to issue the exciting light based on the electric current flowing from the light source driver 26 in response to the intensity modulated signal as determined in the FG 24. The exciting light issued from the light source 12 enters the optical unit for incident light 14, where it is rendered parallel by the collimator lens 30, partially blocked by the light shield plate 36, then condensed by the cylindrical lens 32 in only one direction, and thereafter polarized by the polarizing filter 34.

The light passing through the optical unit 14 is incident on the prism 38, through which it travels as a beam having a specified angular range until it reaches the boundary surface between the prism 38 and the metal film 40; the light is then reflected totally by the boundary surface between the prism 38 and the metal film 40 to emerge from the prism 38. Note that the cylindrical lens 32 condenses the light in such a way that it is focused at a position a certain distance beyond the boundary surface between the prism 38 and the metal film 40.

As mentioned above, the parallel light generated by the collimator lens 30 is condensed by the cylindrical lens 32 in only one direction and this ensures that the exciting light has the same angle of incidence in a direction parallel to the direction in which the linear portion 46 extends across the boundary surface between the prism 38 and the metal film 40.

As the result of the total reflection of the exciting light that occurs at the boundary surface between the prism 38 and the metal film 40, an evanescent wave penetrates the metal film 40 to appear on the surface where the channel 45 is formed (opposite the surface in contact with the prism 38) and this evanescent wave excites surface plasmons in the metal film 40. The excited surface plasmons produce an electric field distribution on the surface of the metal film 40 to form an area having an enhanced electric field.

On this occasion, the evanescent wave and surface plasmons that have been generated by that portion of the exciting light incident at angles in a specified range which struck the boundary surface between the prism 38 and the metal film 40 at a specified angle (specifically, at the angle that satisfies the plasmon resonance condition) resonate with each other, causing surface plasmon resonance (the plasmon enhancing effect). In the area where this surface plasmon resonance (plasma enhancing effect) has occurred, a more intense enhancement of the electric field is realized. The plasmon resonance condition as referred to above is such a condition that the wavenumber of the evanescent wave generated by the incident light becomes equal to the wavenumber of surface plasmons to establish a wavenumber match. As already mentioned, this plasmon resonance condition depends on various factors including the type of the sample, its state, the thickness of the metal film, its density, the wavelength of the exciting light, and its incident angle. Also note that in the invention the plasmon resonance angle and the incident angle of the exciting light refer to the angle formed with respect to the line normal to the metal film.

It should be noted here that if the fluorescent material 86 is present in the area where the evanescent wave has come out, it is excited to generate fluorescence. This fluorescence is enhanced by the field enhancing effect of the surface plasmons that are present in an area substantially comparable to the area where the evanescent wave has come out, particularly by the field enhancing effect as enhanced by the surface plasmon resonance.

Also note that the fluorescent material that is outside the area where the evanescent wave has come out is not excited and hence does not generate fluorescence.

In this way, the fluorescence from the fluorescent material 86 with which the analytes 84 immobilized on the metal film 40 are labeled is excited and enhanced.

The light issued from the fluorescent material 86 is incident on the first lens 56 in the light detecting means 18, passes through the cut-off filter 58, is condensed by the second lens 60, and is launched into the PD 52 where it is converted to an electric signal. Since the component of the light that is incident on the first lens 56 and which has the same wavelength as the exciting light cannot pass through the cut-off filter 58, the exciting light component does not reach as far as the PD 52.

The electric signal generated in the PD 52 is amplified as a detection signal in the PD amp 54 and thence fed into the lock-in amp 64, which amplifies the signal component that is synchronous with the reference signal. As a result, the light originating from the exciting light can be sufficiently amplified that any unwanted noise components (for example, the light that has been launched into the PD 52 other than from the optical unit for detecting light 50, as exemplified by the light from fluorescent lamps in a room or the light from sensors in the apparatus, as well as the dark current generated in the PD 52) can be positively distinguished from the light issued from the fluorescent material 86.

The detection signal amplified by the lock-in amp 64 is sent to the PC 66.

The PC 66 performs A/D conversion on the signal, and based on a preliminarily stored calibration line, it detects the concentration of the analytes 84 in the sample 82 from the result of computation about the analytes 84.

In the manner described above, the sensing apparatus 10 detects the concentration of the analytes 84 in the sample 82.

Figure 6:
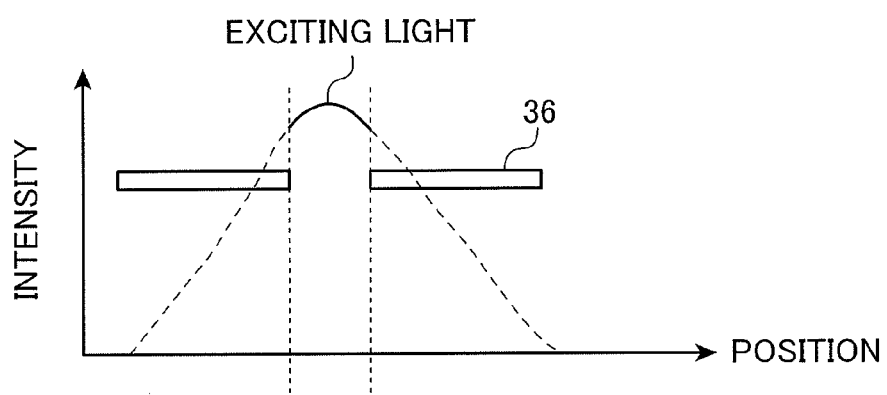
FIG. 6 is a diagram showing the relationship between the intensity of exciting light and a light shield plate in terms of position.
Figure 7:
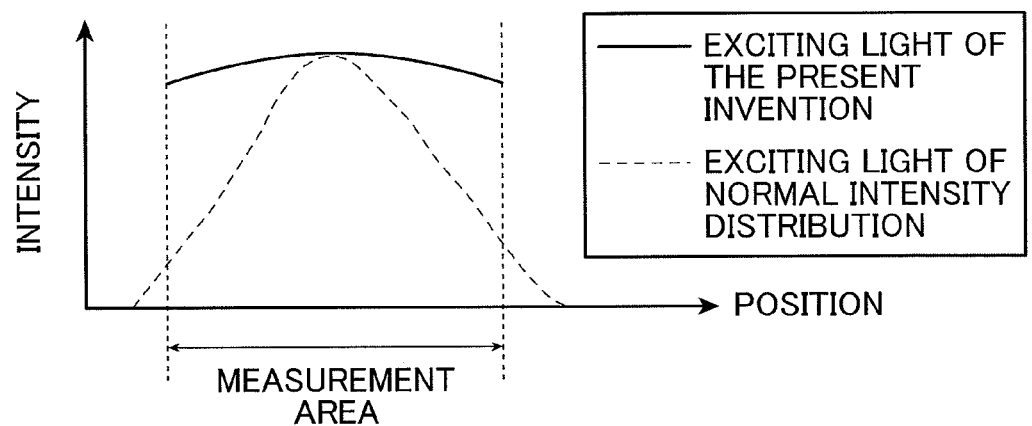
FIG. 7 is a diagram showing the relationship between the position in the measurement area and the intensity of exciting light incident on a detection surface.

Here, FIG. 6 is a diagram showing the relationship between the intensity of exciting light and the light shield plate in terms of position; FIG. 7 is a diagram showing the relationship between the position in the measurement area and the intensity of exciting light incident on the detection surface; and FIGS. 8A and 8B are diagrams each showing the relationship between the intensity of conventional exciting light and the condition for the occurrence of surface plasmon resonance.

In the sensing apparatus 10, the light shield plate 36 which blocks part of the exciting light (specifically, the light more than a certain distance away from the center of the exciting light beam) is provided in the optical unit for incident light 14 and, consequently, as shown in FIG. 6, only the intense portion of the exciting light that is near the center of the light beam (the light indicated by the solid line in FIG. 6) passes through the opening formed in the light shield plate 36 but the less intense portions in the other regions (the light indicated by the dotted line in FIG. 6) are blocked by the light shield plate 36.

It should be noted here that the light issued from the light source 12 has a normal distribution, so if it is simply condensed and allowed to be incident as the exciting light, the light incident in the measurement area of the boundary surface between the prism 38 and the metal film 40 (this area is hereinafter sometimes referred to simply as the "measurement area") is such that its intensity varies greatly between maximum and minimum values, as indicated by the dotted line in FIG. 7.

To deal with this problem, the sensing apparatus 10 incorporates the light shield plate 36 so that the exciting light that arrives at the boundary surface between the prism 38 and the metal film 40 can be processed to have a smaller intensity distribution, as indicated by the solid line in FIG. 7. In short, one can obtain light having a small enough difference in intensity between its maximum and minimum values.

This possibility of allowing the exciting light with a smaller intensity distribution to be incident in the measurement area offers the following advantage: even if the plasmon resonance angle varies (or fails to satisfy the plasmon resonance condition) for each sample unit, the exciting light has almost no difference in intensity, so the enhanced electric field (to be more exact, the enhanced electric field that is generated on account of surface plasmons) has substantially the same intensity (namely, the difference in intensity is small).

Let us explain this in greater detail. If light such as one with a normal distribution that has differences in intensity depending on the angle of incidence is used as the exciting light, the intensity of the exciting light that contributes to surface plasmon resonance varies greatly with the plasmon resonance angle.

Here, FIGS. 8A and 8B show how exciting light of normally distributed intensity varies in terms of intensity distribution under different conditions; in FIG. 8A, the intensity distribution of the exciting light in the case where a ray of light near the center of the exciting light beam is incident on the metal film 40 at an angle that agrees with the plasmon resonance angle θ1 is indicated by a curve 90, and the intensity distribution of the exciting light after it is totally reflected at the boundary surface between the prism 38 and the metal film 40 is indicated by a curve 92; in FIG. 8B, the intensity distribution of the exciting light in the case where a ray of light away from the center of the exciting light beam is incident on the metal film 40 at an angle that agrees with the plasmon resonance angle θ2 is indicated by a curve 90', and the intensity distribution of the exciting light after it is totally reflected at the boundary surface between the prism 38 and the metal film 40 is indicated by a curve 92'.

As FIG. 8A shows, when surface plasmon resonance is caused to occur by the light incident at the plasmon resonance angle θ1, a ray of light near the peak of the intensity distribution curve 90 (the light component with the intensity marked off by the circle in FIG. 8A) is converted to surface plasmon resonance. In contrast, as FIG. 8B shows, when surface plasmon resonance is caused to occur by the light incident at the plasmon resonance angle θ2, a ray of light in the middle of the descending slope of the intensity distribution curve 90' (the light component with the intensity marked off by the circle in FIG. 8B) is converted to surface plasmon resonance. As a result, the intensity of the light that contributes to the surface plasmon resonance takes on greatly different values. Consequently, the intensity of the reflected light in the former case drops by a greater amount than that in the latter case, as is apparent from the two intensity distribution curves 92 and 92'. In other words, the plasmon resonance angle θ1 contributes more to surface plasmon resonance than the plasmon resonance angle θ2 does, with the result that more energy is converted to surface plasmons.

With such a great difference in the intensity of the light that is converted to surface plasmon resonance, the surface plasmons generated also have a great difference in intensity. Specifically, the case shown in FIG. 8A produces more intense surface plasmons than the case shown in FIG. 8B.

On the other hand, the sensing apparatus 10 involves almost no difference in the intensity of exciting light (to be more exact, it involves only a small difference in the intensity of exciting light), namely, a ray of light near the center of the exciting light beam has almost no difference in intensity from a ray of light distant from the center of the exciting light beam; hence, whichever angle of the incident exciting light coincides with the plasmon resonance angle, the difference in the amount of energy of the exciting light that contributes to surface plasmon resonance and, hence, the difference in the intensity of surface plasmons generated on the metal film, can be sufficiently reduced to ensure that enhanced electric fields having a substantially uniform intensity can be produced on the metal film.

Thus, enhanced electric fields of a substantially uniform intensity can be produced on the metal film irrespective of the plasmon resonance angle and this contributes to constancy in the enhanced electric fields that enhance the fluorescence from the fluorescent material. Consequently, even if sample units having different plasmon resonance angles are used to perform measurements, detection signals of constant intensity can be obtained for the same number and concentration of analytes.

As a result, highly reproducible measurements can be performed and the number and concentration of analytes can be correctly detected (or measured).

In addition, the absence of the need to detect the plasmon resonance angle enables the detection job to be completed within a short period of time. As a further advantage, there is no need to perform pre-measurement excitation of the fluorescent material for the purpose of setting initial conditions, so it is also possible to prevent a drop in the intensity of light emission.

The plasmon resonance angle also varies with the sample to be positioned on the metal film or the analyte in the sample; however, with the sensing apparatus of the present invention, light diffusing through a certain angular range can be allowed to be incident at substantially constant intensities, so even if the plasmon resonance angle varies on account of using different samples or different analytes, there is no need to perform angle adjustment and detection can be accomplished by the same apparatus.

For example, a single sensing apparatus may be used to detect analytes in two different samples, one being urine and the other being blood.

Thus, the present invention enables more diverse substances to be detected than in the prior art. Further in addition, enhanced electric fields of uniform intensity can be produced on the metal film irrespective of the plasmon resonance angle and this contributes to ensuring that detection precision will not fluctuate with the substance to be detected.

On the following pages, the present invention will be described in detail together with a specific example.

Figure 9:
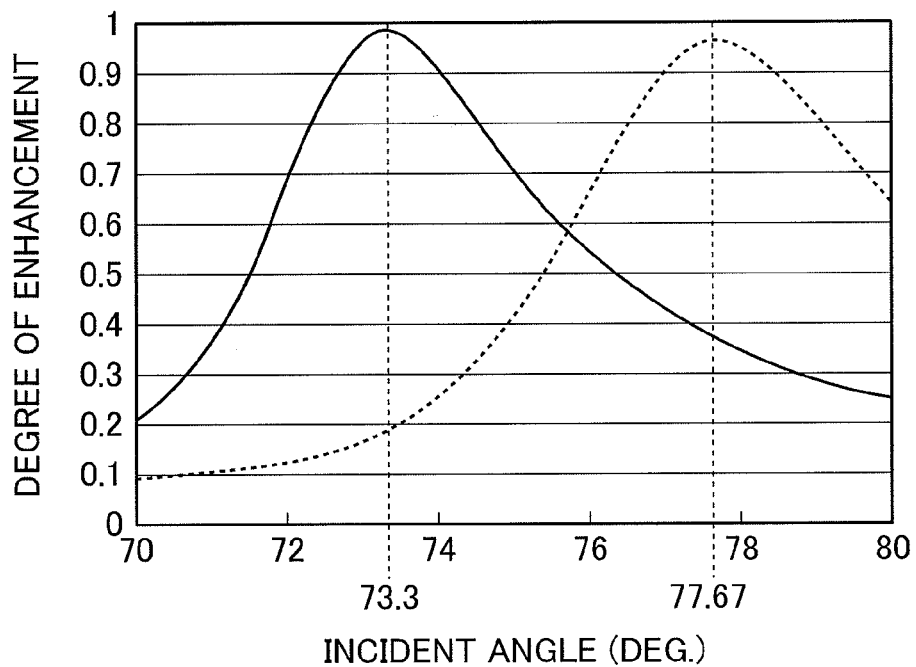
FIG. 9 is a graph showing the relationship between the angle of incidence and the degree of enhancement in the case of using whole blood and urine as samples.
Figure 10:
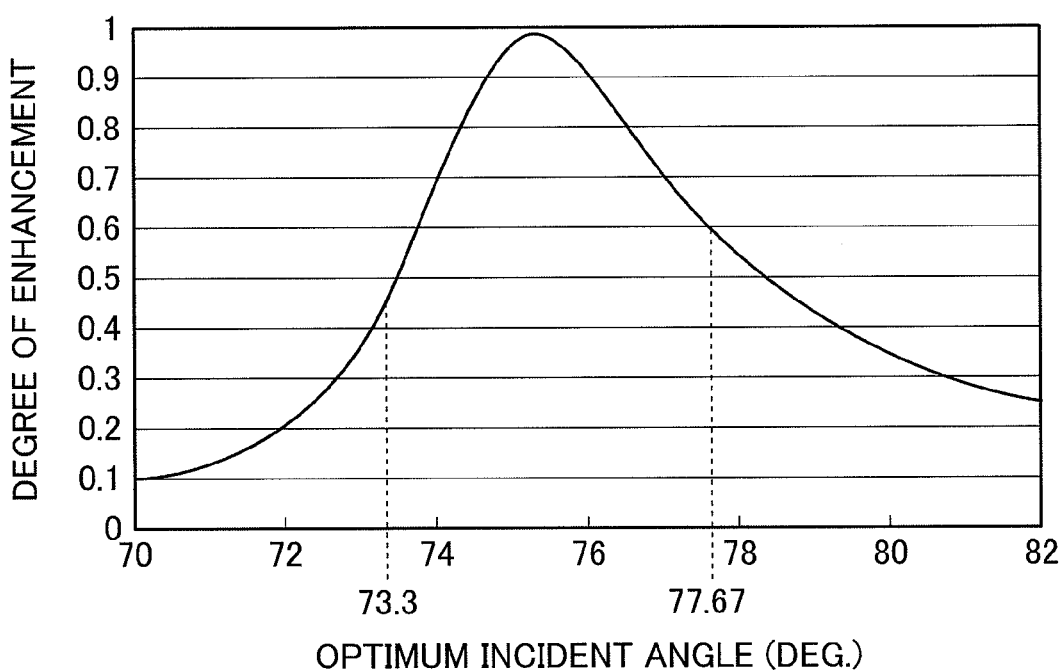
FIG. 10 is a graph showing the relationship between the optimum angle of incidence on the sample unit and the degree of enhancement that occurs when light is incident on the sample at specified angles of incidence.
Figure 11:
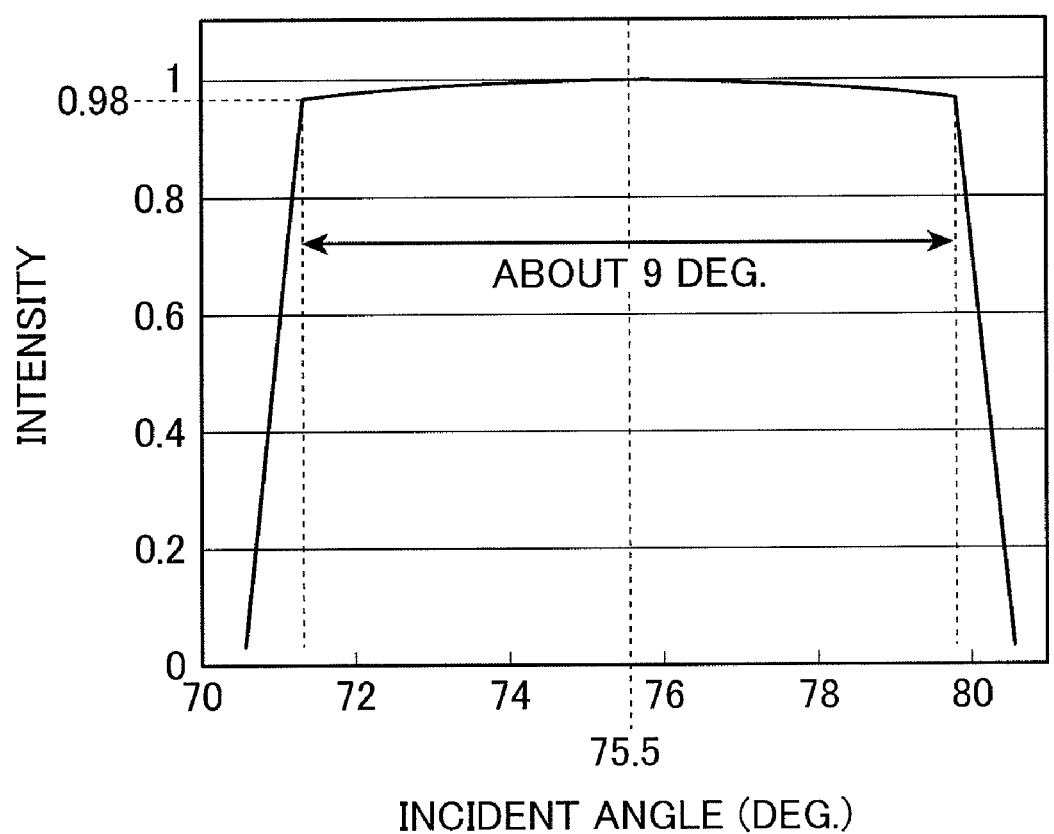
FIG. 11 is a graph showing the relationship between the angle of incidence of exciting light (incident light) at the boundary surface and the intensity of the exciting light.

Here, FIG. 9 is a graph showing the relationship between the angle of incidence and the degree of enhancement in the case of using whole blood and urine as samples; FIG. 10 is a graph showing the relationship between the angle of incidence on a sample and the degree of enhancement, the sample developing a maximum degree of enhancement of surface plasmons when light is incident at 75.5 degrees which is intermediate between the optimum angles of incidence on the two samples illustrated in FIG. 9; and FIG. 11 is a graph showing the relationship between the angle of incidence of exciting light (incident light) at the boundary surface and the intensity of the exciting light.

Take, for example, the case of preparing sample units of basically the same construction (the prism being prepared from PMMA (polymethyl methacrylate)); whole blood and urine cause the refractive indices of the sample units to fluctuate over the range from 1.335 to 1.36 depending on the differences between individuals and physical conditions.

Given exciting light having a wavelength of 656 nm, the relationship that the incident angle of the light launched into the sample unit has with respect to the degree of surface plasmon enhancement (i.e., how much of the incident light is converted to surface plasmons) varies as depicted in FIG. 9 for the two refractive index values of 1.335 and 1.36. To state more specifically, at the refractive index of 1.335, the optimum plasmon resonance angle (the incident angle at which the highest degree of enhancement is attained) is 73.3 degrees whereas at the refractive index of 1.36, the optimum plasmon resonance angle is 77.67 degrees, the variation being about 4.3 degrees.

Since the optimum plasmon resonance angle (i.e., an optimum angle of incidence) thusly varies depending on the individual difference between samples and on the difference in the type of samples, if the exciting light is allowed to be incident at one and the same angle at all times, the intensity by which surface plasmons are enhanced (the degree of their enhancement) will vary, as shown in FIGS. 9 and 10. To be more specific, given the range of fluctuations that are experienced by the sample units, say, at the incident angles of 73.3 degrees and 77.67 degrees, the highest degree of enhancement (see FIG. 9) differs from the lowest degree of enhancement (see FIG. 10) by as much as about 50% irrespective of which incident angle is taken. Consequently, even if light is allowed to be incident at the same angle, the intensity of surface plasmons varies greatly with the individual difference between samples and on the difference in the type of samples. This eventually causes a change in the intensity of the enhanced electric field that is generated on the metal film.

In addition, even if the light issued from the light source is allowed to be incident at angles over a specified range as described before, the intensity of the light varies with the angle, so the intensity of the enhanced electric field that is generated on the metal film changes with the optimum plasmon resonance angle for the particular sample unit.

To deal with this problem, the following experimental setup of the sensing apparatus 10 was constructed: the light source 12 was an LD (laser diode; ML101J21 of Mitsubishi Electric Corporation) that would emit light ($\lambda$=656 nm; 80 mW) through such an angle of radiation that the full width at half maximum was 9.5 degrees in a direction parallel to the junction but 17 degrees in a direction perpendicular to the junction (i.e., in the embodiment under consideration, the direction on the side the light was condensed by the cylindrical lens 32); the collimator lens 30 was SLB-30-100PM of SHIGMA KOKI Co., LTD. having a diameter (D) of 30 mm and a focal length (f) of 100 mm as measured from the center of the lens; the cylindrical lens 32 was CLB-1010-30PM of SHIGMA KOKI Co., LTD. of such a design that the length in the axial direction as well as the length in a direction perpendicular not only to the light beam (or optical axis) but also to its own axis were each about 4.72 mm and that the focal length (f) as measured from the center of the lens was 30 mm; and the light shield plate 36 was one having a 5.0 mm$^\Phi$ hole opened in it. The distance from the light source 12 to the end face of the collimator lens 30 was adjusted to 100 mm.

The light issued from the light source 12 came to have a full width at half maximum of 50.8664 mm upon arrival at the collimator lens 30 and part of it near the center through the optical axis was converted to parallel light. The only part of the collimated light that passed through the 5.0 mm$^\Phi$ hole in the light shield plate 36 was condensed by the cylindrical lens 32 before it was allowed to strike the boundary surface between the prism 38 and the metal film 40.

With the sensing apparatus 10 constructed in the manner described above, the light incident at the boundary surface between the prism 38 and the metal film 40 has a converging angle of about 9 degrees. Consequently, as shown in FIG. 11, the angular range over which incident light can be caused to strike the boundary surface is at least between 72 and 80 degrees centering at 75.5 degrees which is substantially intermediate between 73.3 and 77.67 degrees.

In addition, by blocking the light rays other than those that pass through the 5.0 mm$^\Phi$ hole in the light shield plate 36, only the light of uniform intensity that is near the center of the light beam is utilized to produce such light that its highest and lowest intensities differ by 2%, as shown in FIG. 11. In other words, the light incident at the boundary surface between the prism 38 and the metal film 40 has such an intensity distribution that compared to its highest intensity which is written as 1.0, the lowest intensity of the exciting light is 0.98.

Thus, according to the example under consideration, the light shield plate offers the advantage that light having a 2% difference between the maximum and minimum intensities and an angular range (converging angle) of 9 degrees can be caused to strike the boundary surface between the prism 38 and the metal film 40 and even if the optimum plasmon resonance angle varies by about 4.3 degrees depending on the sample or sample unit as shown in FIG. 9, the fluorescence originating from the analytes in the sample can be detected under the same conditions. To state more specifically, even if the degree of enhancement of surface plasmons changes with the angle of incidence as shown in FIG. 9, light of all angular components within the region of higher degrees of enhancement can be caused to be incident at substantially uniform intensities, and, as the result, surface plasmons of substantially uniform intensities can be generated irrespective of the optimum angle of incidence for each sample.

The change in the plasmon resonance angle and the offset in the angle of incidence can be caused by other factors than the state of the sample and they are an angular offset in the light issued from the light source, an offset in the mounting of the sample unit, a dimensional error, a refractive index difference in the prism, thermal expansion, and thermal shrinkage, but none of these factors will cause an offset greater than 1 degree. Therefore, the incidence of light in the embodiment under consideration offers the advantage that even if any offset occurs from one of the factors mentioned above, the fluorescence originating from the analytes in the sample can be detected under the same conditions. For instance, even if the light issued from the light source 12 deviates by an angle of 0.3 degrees, the resulting error will not exceed 0.5% and even if the refractive index difference in the prism deviates by 0.6 degrees, the resulting error will not exceed 1%.

The fundamental advantages of the present invention will be apparent from the foregoing explanation.

According to the present invention, highly reproducible measurements can be accomplished using sample units that have different plasmon resonance angles and this contributes to increasing the errors that can be tolerated by sample units, which therefore can be manufactured at lower cost.

In addition, the simple design of providing the light shield plate is sufficient to enable both the number and concentration of the analytes in the sample to be detected (or measured) in a correct way, so a less expensive apparatus can be constructed than in the case of using a rotating mechanism and the like.

In the embodiment under consideration, the light shield plate is provided between the collimator lens and the cylindrical lens; however, the position for mounting the light shield plate is not particularly limited as long as it is in the optical path of the exciting light between the light source and the sample unit and it may be positioned closer to the light source than the collimator lens is or, alternatively, it may be positioned closer to the prism than the cylindrical lens is. The size of the opening to be formed in the light shield plate (namely, the range of the light that can pass through) may be determined by the position of the light shield plate in the optical path and by the difference between the maximum and minimum intensities of the light that is incident at the boundary surface between the prism and the metal film.

Further in addition, the light shield plate is preferably positioned in such a way that it will block light of an intensity less than 98% of the maximum intensity of the light issued from the light source, as illustrated in the foregoing specific example. In other words, it is preferred that the minimum intensity of the light that has passed through the light shield plate is at least 98% of its maximum intensity. By using the light shield plate to block light of an intensity less than 98% of the maximum intensity, one can generate exciting light that has an even smaller difference in intensity and, as a result, the analytes in the sample can be detected or measured in a more correct manner.

As mentioned above, the light shield plate preferably blocks light of an intensity less than 98% of the maximum intensity since this enables more correct detection or measurement of the analytes. However, this specification is simply determined by the particular application of diagnosis and the present invention is by no means limited to this particular case; in another application where a 5% error is tolerated, the light shield plate may be so designed as to block light of an intensity less than 95% of the maximum intensity, with the result that the advantage of the present invention, i.e., forming an electric field of a constant intensity, can indeed be assured.

In the foregoing embodiment, the sensing apparatus 10 has the light shield plate as the light intensity distribution adjusting section to adjust the intensity distribution of the exciting light, but the present invention is by no means limited to this particular case.

Figure 13:
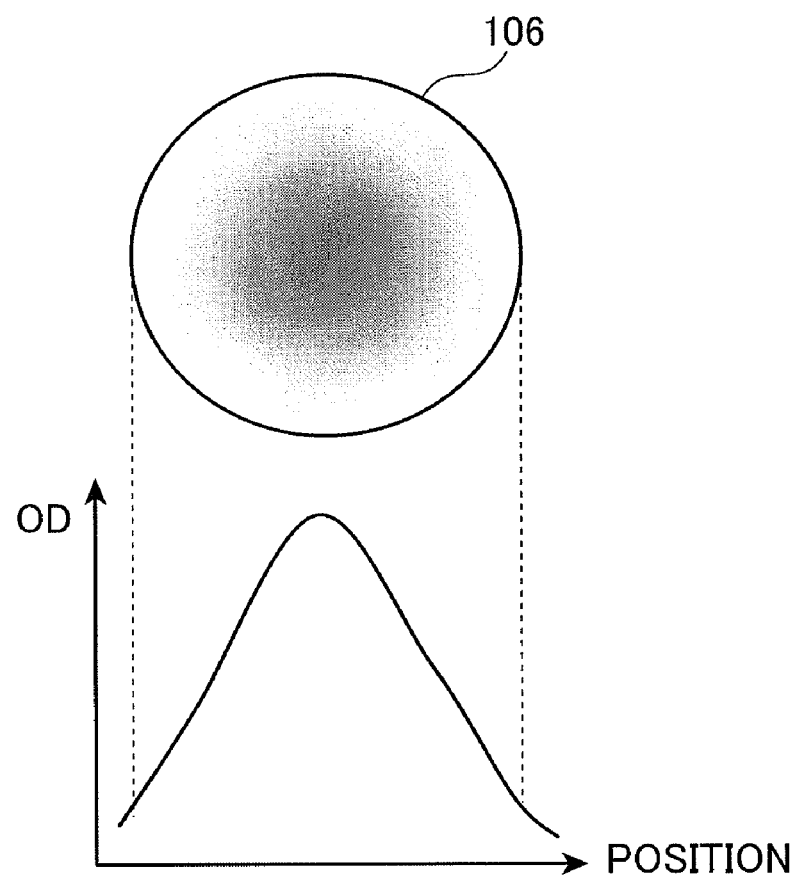
FIG. 13 is an illustration that shows schematically an inverse Gaussian filter in the sensing apparatus shown in FIG. 12.
Figure 12:
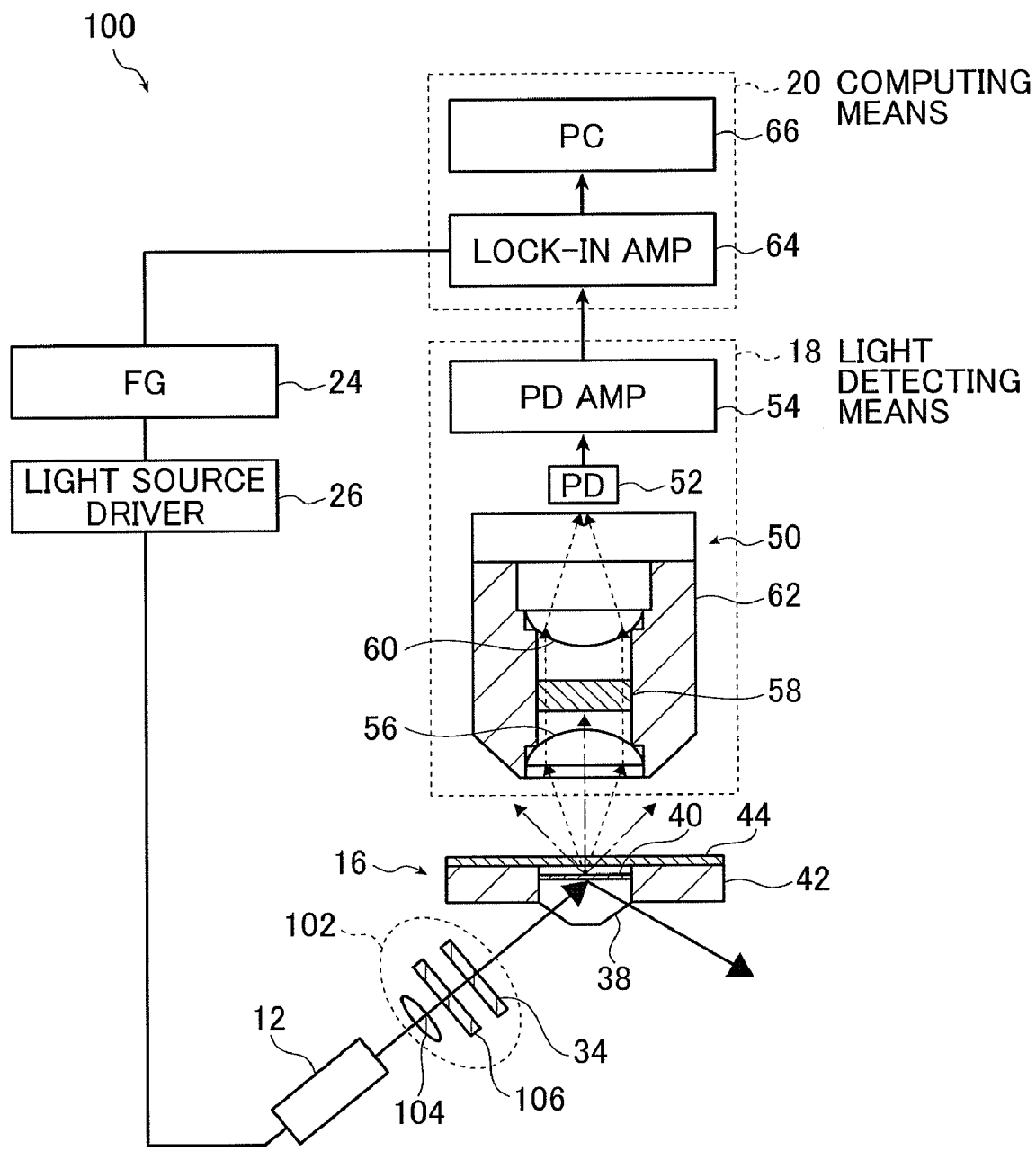
FIG. 12 is a block diagram showing a general construction of another embodiment of the sensing apparatus of the present invention.

On the following pages, another embodiment of the sensing apparatus of the present invention is described with reference to FIGS. 12 and 13. FIG. 12 is a block diagram showing a general construction of a sensing apparatus 100 which is another embodiment of the sensing apparatus of the present invention, and FIG. 13 is an illustration (specifically comprising a front view and a graph) that shows schematically an inverse Gaussian filter 106 in the sensing apparatus 100 shown in FIG. 12.

Here, the sensing apparatus 100 is constructed in the same way as the sensing apparatus 10 shown in FIG. 1, except for the structure of an optical unit for incident light 102 and, therefore, the same constituents are identified by like numerals and will not be described in detail and the following explanation is focused on the particular aspects of the sensing apparatus 100.

As shown in FIG. 12, the sensing apparatus 100 comprises basically a light source 12 that issues light of a specified wavelength, the optical unit for incident light 102, a sample unit 16, a light detecting means 18, and a computing means 20. Like the sensing apparatus 10, the sensing apparatus 100 further includes an FG 24 and a light source driver 26.

The optical unit for incident light 102 comprises a condenser lens 104, an inverse Gaussian filter 106, and a polarizing filter 34, which are inserted into the optical path of the exciting light and arranged in the order written, with the condenser lens 104 being positioned the closest to the light source 12. Hence, the light issued from the light source 12 passes through the condenser lens 104, inverse Gaussian filter 106, and the polarizing filter 34 in that order and is then launched into the sample unit 16. Here, the polarizing filter 34 has the same structure as the polarizing filter 34 in the above-described sensing apparatus 10 and will not be described in detail.

The condenser lens 104 is a device by which the light issued from the light source 12 to diffuse radially through a specified angle is condensed. Note that the condenser lens 104 also condenses the incident light in such a way that it is focused at a position a certain distance beyond the boundary surface between the prism 38 and the metal film 40.

The inverse Gaussian filter 106 is a filter whose optical density (OD) draws a normal distribution curve and increases toward the center which coincides with the center of the light beam (namely, this is a filter whose transmittance decreases toward the center which coincides with the center of the light beam); this filter absorbs the incident exciting light by an increased proportion as it passes through areas that are closer to the center which coincides with the center of the light beam.

Here, the exciting light has such an intensity distribution that it becomes more intense toward the center of the light beam, so by absorbing the incident exciting light by an increased proportion as it passes through the inverse Gaussian filter 106 in areas that are closer to the center which coincides with the center of the light beam, the intensity distribution of the exciting light can be rendered almost constant (to be more exact, the difference between the maximum and minimum intensities can be reduced).

Thus, using the inverse Gaussian filter as the light intensity distribution adjusting section is another way of rendering the intensity distribution of the exciting light almost constant and the same effect is achieved as with the above-described sensing apparatus 10.

A word must be added about use of the inverse Gaussian filter; since this results in a lower maximum intensity, the intensity of the exciting light will become smaller than in the case of using the light shield plate to block part of the exciting light but, on the other hand, a more uniform intensity distribution can be realized than when the light shield plate is used.

As a further advantage, light sources of high intensity are comparatively inexpensive, so the apparatus can be fabricated at low enough cost even if the intensity of exciting light is rendered uniform by means of the inverse Gaussian filter.

While the sensing apparatus according to the present invention has been described above in detail, the present invention is by no means limited to the foregoing embodiments and it should be understood that various improvements and modifications are possible without departing from the scope and spirit of the present invention.

For example, the light intensity distribution adjusting section may be comprised of both a light shield plate and an inverse Gaussian filter such that light of an intensity lower than a certain value is blocked by the light shield plate to reduce the difference between the maximum and the minimum intensities and, thereafter, the emerging light is allowed to pass through the inverse Gaussian filter to produce exciting light of an even smaller difference in intensity. Reducing the difference between the maximum and the minimum intensities by means of the light shield plate offers another advantage in that a smaller amount of light is absorbed by the inverse Gaussian filter, which contributes to maintaining the intensity of the exciting light at high level.

In the sensing apparatus 10 or the sensing apparatus 100, the optical unit for incident light uses a cylindrical lens or a condenser lens to condense the light issued from the light source; this is not the sole case of the present invention and the light issued at a specified angle of radiation from the light source need not be condensed but it may simply be caused to strike the boundary surface between the prism and the metal film. Even in this case where light radiating through a specified angle is allowed to strike the boundary surface, light having a specified angular range can be allowed to strike the boundary surface, and by providing the light intensity distribution adjusting section, light having a smaller intensity distribution can be produced, with the result that the above-described advantages of the present invention can be obtained.

There is also no absolute need to provide the polarizing filter and this is particularly true in the case of using a laser light source since the light issued from the laser is already polarized.

In each of the foregoing embodiments, the number or concentration of the analytes contained in the sample is detected but this is not the sole case of the present invention and one may check to see if the sample contains the analyte or not (i.e., if the analyte is present in the sample or not).

In each of the foregoing embodiments, the analytes are detected by detecting the fluorescence from the fluorescent material as enhanced by the enhanced electric field generated on the metal film, with the analytes being bound to the secondary antibodies labeled with the fluorescent material; the method of labeling the analytes with the fluorescent material is not particularly limited and there is no need to provide secondary antibodies if the analytes themselves are the fluorescent material.

The sensing apparatus of the present invention may also be adapted to detect scattered light that occurs when surface plasmons are generated on the metal film as it has the analytes attached thereto (or positioned in its neighborhood).

In this case of detecting scattered light, the analytes are preferably metal particles which are a strong scatterer. To put this in other words, if the analytes are strongly scattering metal particles, it is preferred to detect scattered light.

The analytes, being strongly scattering metal particles, can be detected more positively.

In each of the foregoing embodiments, an evanescent wave and surface plasmons are generated on the surface of the metal film and, furthermore, surface plasmon resonance is caused to occur to form an enhanced electric field; however, this is not the sole case of the present invention and it may be applied in various approaches in which the degree of enhancement varies with the angle of incidence of light on the surface where the enhanced electric field is to be formed (namely, the enhanced field varies only when light is incident at a specified angle). For example, the present invention is applicable in such an approach that a metal film and a $SiO_2$ film about 1 μm thick are superposed on the prism and that light incident at a specified angle is resonated within the $SiO_2$ film to thereby form an enhanced electric field.

What is claimed is:

1. A sensing apparatus for detecting an analyte in a sample with an aid of an enhanced field that is generated by causing light to strike a detection surface at a specified angle of incidence, comprising:
    a prism;
    a metal film provided on a surface of the prism;
    a substrate that is provided on a surface of the prism and which has formed therein a channel for supplying the sample to the metal film;
    a light source for issuing light;
    an optical unit for incident light by which the light being issued from the light source is launched into the prism at such an angle that the light is totally reflected on a boundary surface between the prism and the metal film to generate an enhanced field on the metal film, the optical unit for incident light including a light intensity distribution adjusting section that reduces difference between the maximum and the minimum values in the intensity distribution of the light that is launched into the prism to make an intensity of the enhanced field generated on the metal film more uniform; and
    a light detecting means for detecting the light emerging from the sample on the metal film.

2. The sensing apparatus according to claim 1, wherein the light intensity distribution adjusting section comprises a light shield member that is provided in an optical path of the light being issued from the light source and which blocks part of the light being issued from the light source.

3. The sensing apparatus according to claim 2, wherein the light shield member blocks light having an intensity of 98% or less of the maximum intensity of the light being issued from the light source.

4. The sensing apparatus according to claim 1, wherein the light intensity distribution adjusting section comprises an absorption filter that is provided in an optical path of the light being issued from the light source and a transmittance of which decreases toward the center which corresponds to the center of the light beam being issued from the light source.

5. The sensing apparatus according to claim 1, further includes a computing means for computing a concentration of the analyte in the sample based on a result of detection by the light detecting means.

* * * * *